(12) United States Patent
Iwasa et al.

(10) Patent No.: US 7,302,787 B2
(45) Date of Patent: Dec. 4, 2007

(54) DEFECT DETECTION DEVICE AND BAG PACKAGING SYSTEM EQUIPPED WITH DEFECT DETECTION DEVICE

(75) Inventors: Seisaku Iwasa, Ritto (JP); Yuji Yokota, Ritto (JP); Yuichiro Minakuchi, Ritto (JP)

(73) Assignee: Ishida Co., Ltd., Kyoto (JP)

( * ) Notice: Subject to any disclaimer, the term of this patent is extended or adjusted under 35 U.S.C. 154(b) by 45 days.

(21) Appl. No.: 11/131,355

(22) Filed: May 18, 2005

(65) Prior Publication Data

US 2005/0277532 A1   Dec. 15, 2005

(30) Foreign Application Priority Data

May 24, 2004   (JP) .............................. 2004-153522

(51) Int. Cl.
*B65B 1/30* (2006.01)
*B65B 57/02* (2006.01)
*B07C 5/10* (2006.01)
*G01N 21/00* (2006.01)

(52) U.S. Cl. .............................. 53/504; 53/76; 493/12; 493/25; 209/586; 209/644; 356/237.1

(58) Field of Classification Search .................. 493/10, 493/12, 16, 17, 25; 53/53, 55, 500, 76, 575, 53/504; 235/492, 435; 209/552, 576, 586, 209/644; 198/493; 356/237.1, 625, 634, 356/635, 638, 639
See application file for complete search history.

(56) References Cited

U.S. PATENT DOCUMENTS

| 2,630,043 | A | | 3/1953 | Kolisch | |
|---|---|---|---|---|---|
| 3,680,692 | A | | 8/1972 | Southworth | |
| 3,837,486 | A | * | 9/1974 | Gardner | 209/564 |
| 4,271,755 | A | * | 6/1981 | Kintgen et al. | 100/52 |
| 4,494,656 | A | * | 1/1985 | Shay et al. | 209/524 |
| 4,722,169 | A | * | 2/1988 | DeSantis | 53/494 |
| 4,998,910 | A | * | 3/1991 | Mohaupt et al. | 493/12 |
| 5,142,159 | A | * | 8/1992 | Veit et al. | 250/559.15 |
| 5,251,422 | A | * | 10/1993 | Goodman et al. | 53/251 |
| 5,524,420 | A | * | 6/1996 | Ikuta | 53/450 |
| 5,740,661 | A | * | 4/1998 | Yamaguchi et al. | 53/553 |

(Continued)

FOREIGN PATENT DOCUMENTS

| GB | 2173302 A | 10/1986 |
|---|---|---|
| JP | 2002-037206 A | 2/2002 |
| JP | 2003-011928 A | 1/2003 |

*Primary Examiner*—Thanh K. Truong
*Assistant Examiner*—Paul Durand
(74) *Attorney, Agent, or Firm*—Global IP Counselors, LLP

(57) ABSTRACT

A bag packaging system includes a bag packager and a defect detection device that receives bags manufactured by the bag packager and conveys the bags while checking for defects. The defect detection device includes a first conveyor belt that is arranged below the bag packager, a line sensor that is arranged adjacent to a downstream end of the first conveyor belt, and a controller. The line sensor sends a detection signal when it detects an object that is conveyed by the first conveyor belt. The controller stores the size of a proper bag that is being manufactured. The controller finds a defective bag based on the size of the proper bag, the conveying speed of the first conveyor belt, and duration of the detection signal from the line sensor. The defect detection device can detect defects in bags promptly after the bags are manufactured by the bag packaging machine.

12 Claims, 12 Drawing Sheets

U.S. PATENT DOCUMENTS 6,000,525 A * 12/1999 Frulio .................. 198/412
6,045,323 A *  4/2000 Achelpohl et al. ....... 414/790.8
6,130,093 A * 10/2000 Dussault et al. ........... 436/47
6,145,668 A * 11/2000 DePauw et al. ........... 209/510
6,164,436 A * 12/2000 Taylor .................. 198/689.1
6,265,683 B1 *  7/2001 Flottmann et al. ......... 209/576
6,683,266 B2 *  1/2004 Maejima ................. 209/587
6,711,874 B1 *  3/2004 Nakagawa et al. ............ 53/64
2002/0014055 A1  2/2002 Iwasa et al.

* cited by examiner

Normal state

Defect 1: Bag with irregular size

Defect 2: Bag with irregular size

Defect 3: Contents spilled out

Defect 4: Interval too narrow

DEFECT DETECTION DEVICE AND BAG PACKAGING SYSTEM EQUIPPED WITH DEFECT DETECTION DEVICE

BACKGROUND OF THE INVENTION

Field of the Invention

The present invention relates to a defect detection device and a bag packaging system equipped with the defect detection device. More specifically, the present invention relates to a defect detection device that is arranged downstream of a bag packaging machine and determines defects of bags while receiving and conveying the bags manufactured by the bag packaging machine.

In recent years, there have been provided bag packaging machines that manufacture bags automatically by thermally sealing a portion of sheet-like package and enclose contents such as snack foods in such bags in order to make bag products.

For bag products manufactured by such bag packaging machines, various approaches are taken to control the bags that are conveyed downstream in order to prevent defective bags from being shipped by mistake. Japanese Patent Application Publication No. 2003-011928 discloses an example of such arrangement.

For example, Japanese Patent Application Publication No. 2002-037206 discloses a longitudinal bag packaging machine that can control the interval and the posture at which and in which the bags are discharged after they are manufactured by and transferred from the bag packaging machine. This longitudinal bag packaging machine is provided with a transport conveyor that conveys the manufactured bags to post-processing devices. By controlling the drive of the transport conveyor, the longitudinal bag packaging machine controls the discharge interval and the discharge posture of the bags that are conveyed. This configuration enables prevention of defect formation in post-processing devices such as a seal checker and a weight checker, while the discharge interval and the discharge posture tend to be compromised where a stationary chute is used instead of a transfer conveyor, particularly when a larger number of bags are discharged at a high processing speed.

However, the above-mentioned conventional devices have the following problems.

Specifically, the longitudinal bag packaging machine disclosed in the Japanese Patent Application Publication No. 2002-037206 simply controls the conveying speed of the transport conveyor in order to control disturbance in the interval and the posture of the bags that are discharged consecutively from the bag packaging machine. Therefore, defective bags caused by sealing failure cannot be detected. Consequently, the defective bags cannot be found at an early point to be removed from the conveyance path, and it is far from an effective process.

In view of the above, it will be apparent to those skilled in the art from this disclosure that there exists a need for an improved defect detection device and an improved bag packaging system that overcome the problems of the conventional art. This invention addresses this need in the art as well as other needs, which will become apparent to those skilled in the art from this disclosure.

SUMMARY OF THE INVENTION

The object of the present invention is to provide a defect detection device, which enables an effective process by promptly detecting defects of bags after the bags are manufactured by the bag packaging machine. The object of the present invention is also to provide a bag packaging system having such defect detection device.

The defect detection device according to the first aspect of the present invention is a defect detection device that is adapted to receive bags manufactured by a bag packaging machine and convey the bags to a downstream side through a conveyance path while checking for defects of the bags. The defect detection device includes a first transfer unit, a detector, and a controller. The first transfer unit is arranged below the bag packaging machine and adapted to receive the bags that are discharged from the bag packaging machine and convey the bags to a downstream side. The detector is arranged adjacent to a downstream end of the first transfer unit and configured to send a detection signal when the detector detects an object that is conveyed by the first transfer unit. The controller is operatively connected to the first transfer unit and the detector, and stores therein a size of a proper bag that is being manufactured. The controller is configured to find a defective bag based on the size of the proper bag, a conveying speed of the first transfer unit, and duration of the detection signal from the detector.

Here, the detector at the downstream end of the first transfer unit below the bag packaging machine detects objects such as the bags and their contents that are discharged and conveyed from the bag packaging machine, and the controller determines whether there is any defective bag.

Since defects of the bags are detected below the bag packaging machine as described above, a prompt detection of the defective bags can be achieved. Consequently, defective bags are prevented from being unnecessarily conveyed to and processed by post-processing devices such as a seal checker that is arranged on the downstream side. Thus, the process efficiency can be improved. Additionally, since a simple sensor that merely detects objects is used as the detector, the defect detection device can be achieved without resulting in much increase in manufacturing cost of the bags.

Further, when the bag packaging machine manufactures the bags that contain food products such as potato chips that have oil content, and when such contents are spilled onto the conveyance path due to sealing failure, the oil tends to soil the conveyance path that extends from the first transfer unit to the downstream side. Therefore, removal of such contents from the conveyance path at an early point, as in the case for the defect detection device of the present invention, can prevent slipping and tipping of the bags and pitch misalignment of the bags during conveyance. This is especially effective when the conveyance path is tilted upward, in which the bags are conveyed upward from upstream side of the first transfer unit to the downstream side, since the bags easily slip on such tilted conveyance path because when the conveyance path is soiled with oil.

It should be noted that the defects of the bags described here include a case where contents of a bag are discharged onto the first transfer unit with a sealing failure, and a case where bags that should be conveyed at predetermined intervals after being manufactured by the bag packaging machine are conveyed one after another at an interval that is too narrow and thus the bags cannot be processed properly by the downstream post-processing devices. The defects further include a case where a double-bag (a bag having a length of two bags) is manufactured due to the reaction of a metal detector that is provided between a weighing machine and a packaging machine of the bag packaging machine, and a case where a bag having other irregular length and irregular size is manufactured due to a setting error.

As the first transfer unit, a conveyor or a chute can be used. Specifically, when a conveyor is used as the first transfer unit, it results in an accurate control of the conveying speed. Thus, defect determination by the controller can be implemented more accurately.

The defect detection device according to the second aspect of the present invention is the defect detection device of the first aspect of the present invention, wherein the detector is arranged so as to be partially below and partially above a conveyance surface of the first transfer unit.

Here, since the detector that detects objects that are conveyed on the first transfer unit is arranged so as to also cover the space below and above the conveyance surface of the first transfer unit, the detector can detect not only a relatively large bag but also contents of a bag that are spilled onto the conveyance surface of the first transfer unit due to a sealing failure.

Because of this configuration, if the detector detects contents of a bag, such as snack foods, bags that are conveyed before or after the detected contents can be detected to be a defective bag in which there has been a sealing failure.

The defect detection device according to the third aspect of the present invention is the defect detection device of the first or the second aspect of the present invention, further including a second transfer unit that is arranged on the downstream side of the first transfer unit.

Here, the defect detection device further includes the second transfer unit that is connected with the first transfer unit and is arranged on the downstream side of the first transfer unit, which is disposed below the bag packaging machine.

This configuration enables a smooth conveyance of the bags to the post-processing devices, which are arranged further downstream of the defect detection device.

The defect detection device according to the fourth aspect of the present invention is the defect detection device of the third aspect of the present invention, wherein the downstream end of the first transfer unit is arranged so as to be above an upstream end of the second transfer unit.

Here, the position of the downstream end of the first transfer unit at the connecting portion between the first and the second transfer units is determined in relation to the position of the upstream end of the second transfer unit, which is arranged on the downstream side of the first transfer unit. In other words, the downstream end of the first transfer unit is arranged so as to be above the upstream end of the second transfer unit at the connecting portion between the first and the second transfer units, thereby creating a step portion between the first and the second transfer units.

This configuration enables the detector to be easily arranged below the imaginary surface that is formed by extending the conveyance surface of the first transfer unit.

The defect detection device according to the fifth aspect of the present invention is the defect detection device of any of the first through the fourth aspects of the present invention, wherein the detector is a line sensor that has a plurality of projectors and a plurality of photoreceivers. The plurality of projectors and a plurality of photoreceivers are arranged such that the object conveyed by the first transfer unit passes between the plurality of projectors and the plurality of photoreceivers.

Here, when a photoreceiver receives light emitted from a projector, no object is detected between the photoreceiver and the projector. On the other hand, when the photoreceiver receive no light, an object is detected between the photoreceiver and the projector.

Because of this, if, for example, the duration of time during which the amount of light received by the photoreceiver has decreased is long compared to the proper interval time period which is calculated based on the conveying speed of the first transfer unit and the size of the proper bag, defects such as overlapping or unsevered bags will be detected as the bags are conveyed. Therefore, the defective bags that are conveyed by the first transfer unit are detected with an inexpensive and simple composition.

The defect detection device according to the sixth aspect of the present invention is the defect detection device according to one of the first through the fifth aspects of the present invention, wherein the first transfer unit has a conveying belt that conveys the object and a motor that rotates the conveying belt.

Here, since a conveyor is used as the first transfer unit, the conveying speed can be easily controlled. Additionally, since objects can be conveyed at a more accurate conveying speed as compared to a case where a chute is used as the first transfer unit, a calculation for detection of defects by the controller can be implemented more accurately.

The defect detection device according to the seventh aspect of the present invention is defect detection device according to one of the first through the sixth aspects of the present invention, wherein the first transfer unit is pivotably supported by the second transfer unit.

Here, the first transfer unit can be pivoted around, for example, the vicinity of the downstream end of the first transfer unit, so as to better accommodate the size (length) of the bags manufactured by the bag packaging machine.

This configuration enables the upstream end of the first transfer unit to be lowered to an appropriate height when the bags being manufactured are big, while also enabling the upstream end to be raised to an appropriate height when the bags being manufactured are small. Consequently, even when different types of bags are manufactured, the bags can be conveyed smoothly to the defect detection device and to the post-processing devices downstream.

Further, since the first transfer unit can pivot around, for example, the vicinity of the downstream end of the first transfer unit, the height of the first transfer unit can be changed without making a substantial change to the positional relationship between the detector that is adjacent to the downstream end of the first transfer unit and the downstream end of the first transfer unit. Consequently, even when the height of the first transfer unit is changed, defects can be detected by the detector in a stable manner.

The defect detection device according to the eighth aspect of the present invention is the defect detection device of the third or the fourth aspect of the present invention, wherein the controller is configured to find a defective bag further based on a conveying speed of the second transfer unit.

Here, the controller that determines whether or not detected bags are defective also takes into consideration the conveying speed of the second transfer unit that is arranged downstream of the first transfer unit.

For example, when a bag manufactured by the bag packaging system is long, a front portion of the bag in the conveying direction may be already reaching the second transfer unit and conveyed by the second transfer unit while the bag is being detected by the detector. Therefore, when the size (length) of a bag is long, more accurate defect determination can be achieve by taking into account the conveying speed of the second transfer unit and the duration of the detection signal from the detector.

The defect detection device according to the ninth aspect of the present invention is the defect detection device according to any of the first through the eighth aspects of the present invention, further including a remover that removes object from the conveyance path when the controller finds a defective bag.

Here, the defect detection device further includes the remover that removes the bags determined to be defective by the controller and the contents that spilled onto the conveyance path from the conveying surface of the first transfer unit.

This configuration enables removal of the defective bags and the contents spilled onto the conveying surface due to a sealing failure before such bags and contents are conveyed to the post-processing devices arranged on the downstream side of the defect detection device. By removing the defective bags before they go through the post-processes, unnecessary processes can be avoided, thereby improving the process efficiency.

The defect detection device according to the tenth aspect of the present invention is the defect detection device of the ninth aspect of the present invention, wherein the remover is adapted to remove the object from the conveyance path by blowing air onto the object.

Here, a device such as an air jet that blows air onto an object is utilized as the remover to remove from the conveyance path the defective bags and the contents that spilled onto the conveyance path.

This configuration enables the defective bags and the contents that spilled onto the conveyance path due to sealing failure to be removed from the conveyance path in a reliable manner with an inexpensive composition.

The defect detection device according to the eleventh aspect of the present invention is the defect detection device of the ninth or tenth aspect of the present invention, further including a second transfer unit that is arranged on the downstream side of the first transfer unit, and in which the remover is adapted to remove the object from the conveyance path while the object is being conveyed by the second transfer unit.

The defect detection device according to the twelfth aspect of the present invention is the defect detection device of the seventh aspect of the present invention, in which the first transfer unit is supported to the second transfer unit so as to be pivotable around the downstream end of the first transfer unit.

The defect detection device according to the thirteenth aspect of the present invention is the defect detection device of any of the first though the twelfth aspects of the present invention, in which the controller is configured to calculate a proper detection time range based on the size of the proper bag and the conveying speed of the first transfer unit, and the controller is configured to find a defective bag when the duration of the detection signal is either longer or shorter than the proper detection time range.

The defect detection device according to the fourteenth aspect of the present invention is the defect detection device of any of the first though the thirteenth aspects of the present invention, in which the controller is configured to calculate a proper interval time period based on the size of the proper bag and the conveying speed of the first transfer unit, and the controller is configured to find a defective bag when an interval between the detection signals is shorter than the proper interval time period.

The bag packaging system according to the fifteenth aspect of the present invention includes a bag packaging machine that manufactures bags by sealing a sheet-like package paper and forming bags with contents contained therein, and the defect detection device according to any of the first through fourteenth aspects of the present invention that is designed to receive bags manufactured by the bag packaging machine and convey the bags to a downstream side through a conveyance path while checking for defects of the bags.

Here, the detector at the downstream end of the first transfer unit that is disposed below the bag packaging machine detects the bags and their spilled contents discharged that are conveyed from the bag packaging machine, so that the controller can find defects.

In this way, since defects can be detected below the bag packaging machine, it is possible to detect the defective bags at an early point. This prevents the defective bags from being unnecessarily conveyed to and processed by the downstream post-processing devices such as a seal checker, thus improving the process efficiency. Additionally, since a simple sensor that merely detects objects is used as the detector, it is possible to provide a bag packaging system that can detect defective bags without much increase in the cost.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

A bag packaging system 1 provided with the defect detection device according to an embodiment of the present invention will be now described with reference to FIGS. 1 to 12.

Entire Configuration of Back Packaging System

Figure 1:
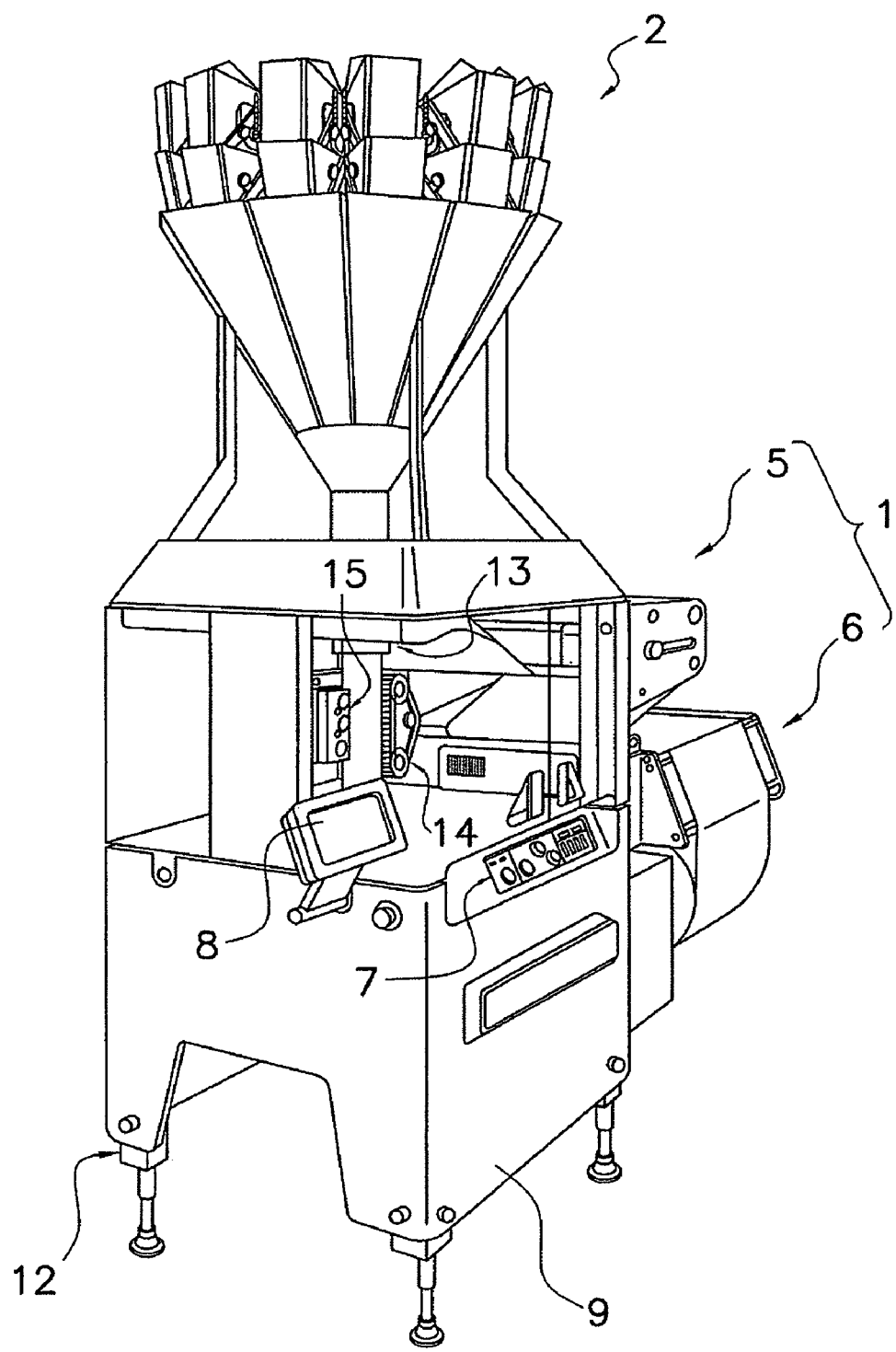
FIG. 1 is a perspective view of a bag packaging system in accordance with an embodiment of the present invention.
Figure 2:
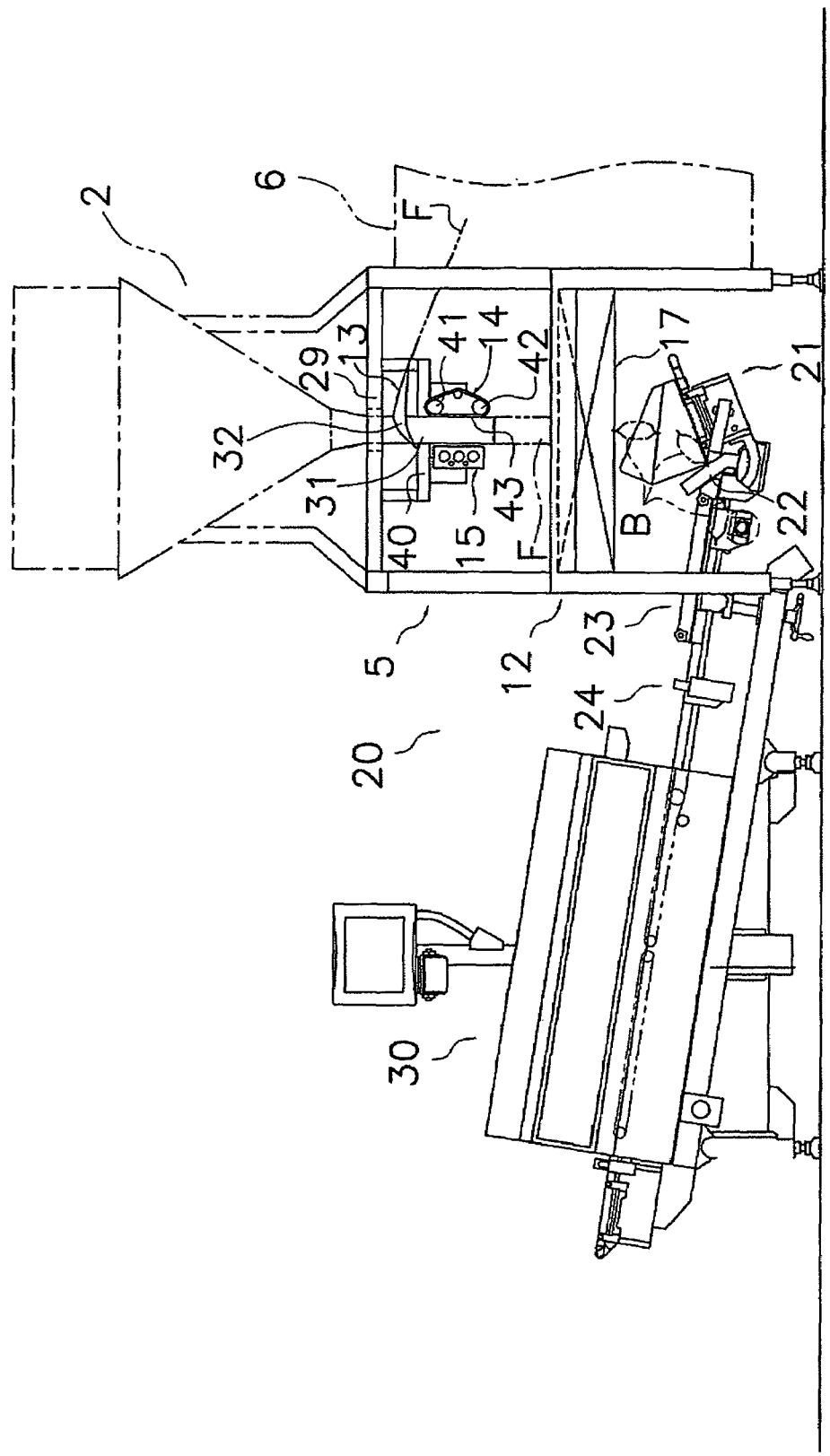
FIG. 2 is a side view of the bag packaging system in accordance with the embodiment of the present invention.

As shown in FIGS. 1 and 2, the bag packaging system 1 according to the embodiment of the present invention is a machine that packages such contents as potato chips, and mainly includes a bag packager (bag packaging machine) 5 that serves as the main section where the contents to be packaged are put into bags, a film feeder 6 that feeds film to the bag packager 5 for making the bags, and a defect detector (an example of the defect detection device) 20 that detects the defective bags while conveying the bags manufactured by the bag packager 5 to post-processing devices such as a seal checker 30 in the subsequent process. An operating switch 7 is arranged on the front panel of the bag packager 5. A liquid crystal display 8 that indicates the operating state is arranged in a position where it can be viewed by an operator operating the operating switch 7.

Configurations of Film Feeder and Bag Packager

The film feeder 6 serves to feed sheet-like film to a forming mechanism 13 of the bag packager 5 and, in this embodiment, is provided adjacent to the bag packager 5. A roll of film is set in the film feeder 6 and the film is discharged from the roll.

As shown in FIGS. 1 and 2, the bag packager 5 includes a forming mechanism 13 that forms the film (which is fed in sheet form) into a tubular form, a pull-down belt mechanism (packaging material conveying mechanism) 14 that conveys the tubular-formed film (hereinafter called "tubular film") downward, a longitudinal sealing mechanism 15 that longitudinally heat-seals an overlapping section of the tubular film, a transverse sealing mechanism 17 that transversely seals the tubular film so as to close the top and bottom ends of the bag, and a support frame 12 that supports these mechanisms. A casing 9 is installed around the support frame 12.

As shown in FIG. 2, the forming mechanism 13 has a tube 31 and a former 32. The tube 31 is a cylindrical member that is open at its upper and lower ends. In a plan view, the tube 31 is arranged in an open portion near the center of a ceiling plate 29 and is integrally joined with the former 32 by a bracket not shown in the figures. A combination weighing machine 2 weighs a predetermined quantity of contents and supplies the predetermined quantity of contents to be packaged into the upper opening of the tube 31. The former 32 is arranged so as to surround the tube 31. The former 32 is shaped such that the sheet-like film F fed from the film feeder 6 is formed into a tubular form as it passes between the former 32 and the tube 31. The former 32 is fixedly supported to the support frame 12 by a support member not shown in the figures. The tube 31 and former 32 of the forming mechanism 13 are constituted such that they can be exchanged with other tubes and formers depending on the width of the bags being made. Consequently, the forming mechanism 13 are disposed within the support frame 12 so as to be freely attached to and detached from the support frame 12.

The pull-down belt mechanism 14 and the longitudinal sealing mechanism 15 are supported by a rail 40 so as to hang down from the ceiling plate 29. The pull-down belt mechanism 14 and the vertical sealing mechanism 15 are arranged so as to sandwich the tube 31 from both sides. These mechanisms 14, 15 are moved along the rail 40 and positioned accordingly when the tube 31 is installed. The pull-down belt mechanism 14 is a mechanism that uses vacuum suction to hold onto the tubular film F wrapped around the tube 31 and conveys the film downward. The pull-down belt mechanism 14 mainly includes a drive roller 41, a driven roller 42, and a belt 43 that has a vacuum-holding function. The longitudinal sealing mechanism 15 longitudinally seals an overlapped portion of the tubular film wrapped around the tube 31 by applying heat while pressing the overlapping portion of the tubular film against the tube 31 with a constant pressure. The longitudinal sealing mechanism 15 has a heated belt or the like that is heated by a heating element and contacts the overlapping portion of the tubular film.

Configuration of Transverse Sealing Mechanism

Now the transverse sealing mechanism 17 will be described.

Figure 3:
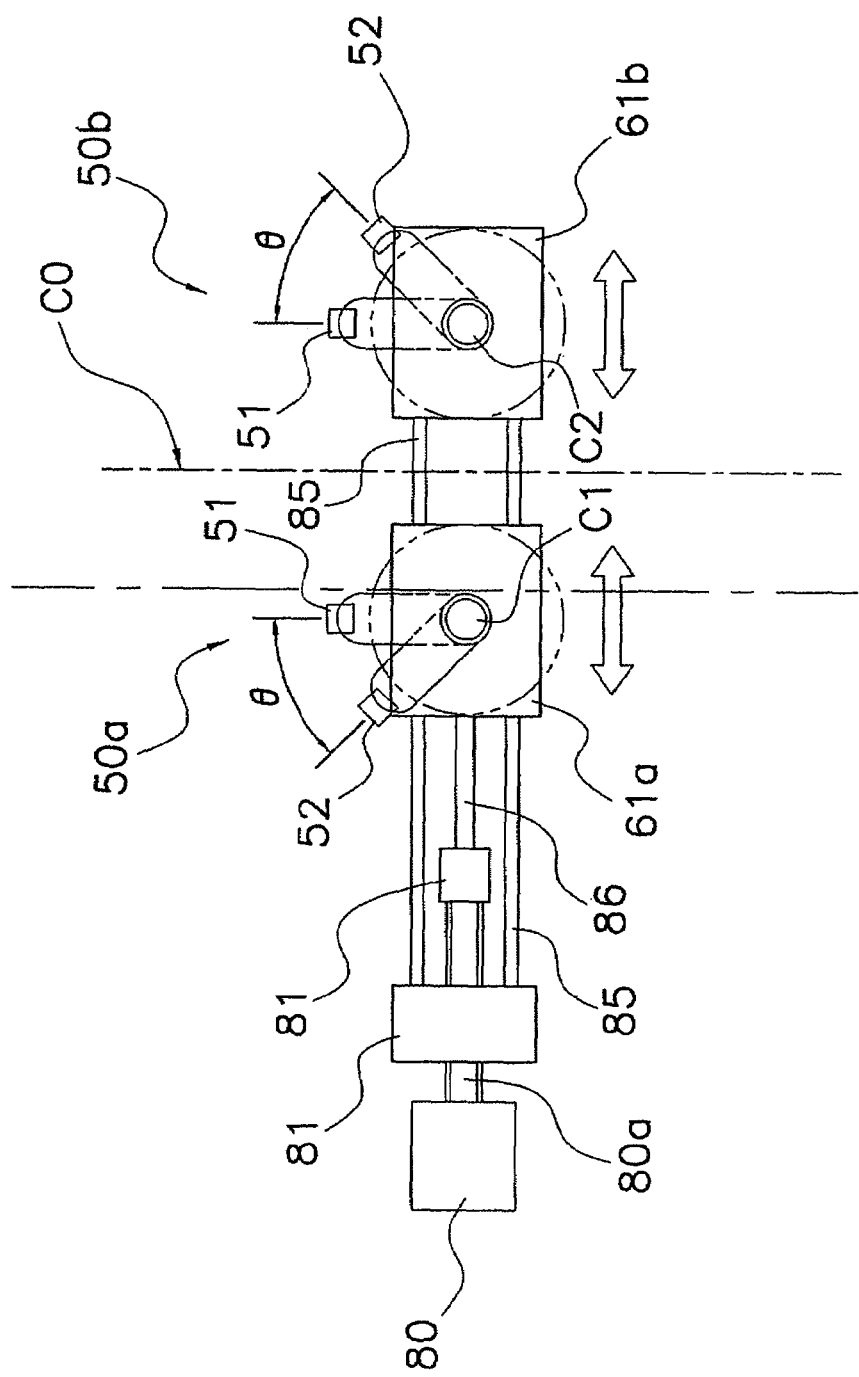
FIG. 3 is a side view of a transverse sealing mechanism of the bag packaging system in accordance with the embodiment of the present invention.
Figure 4:
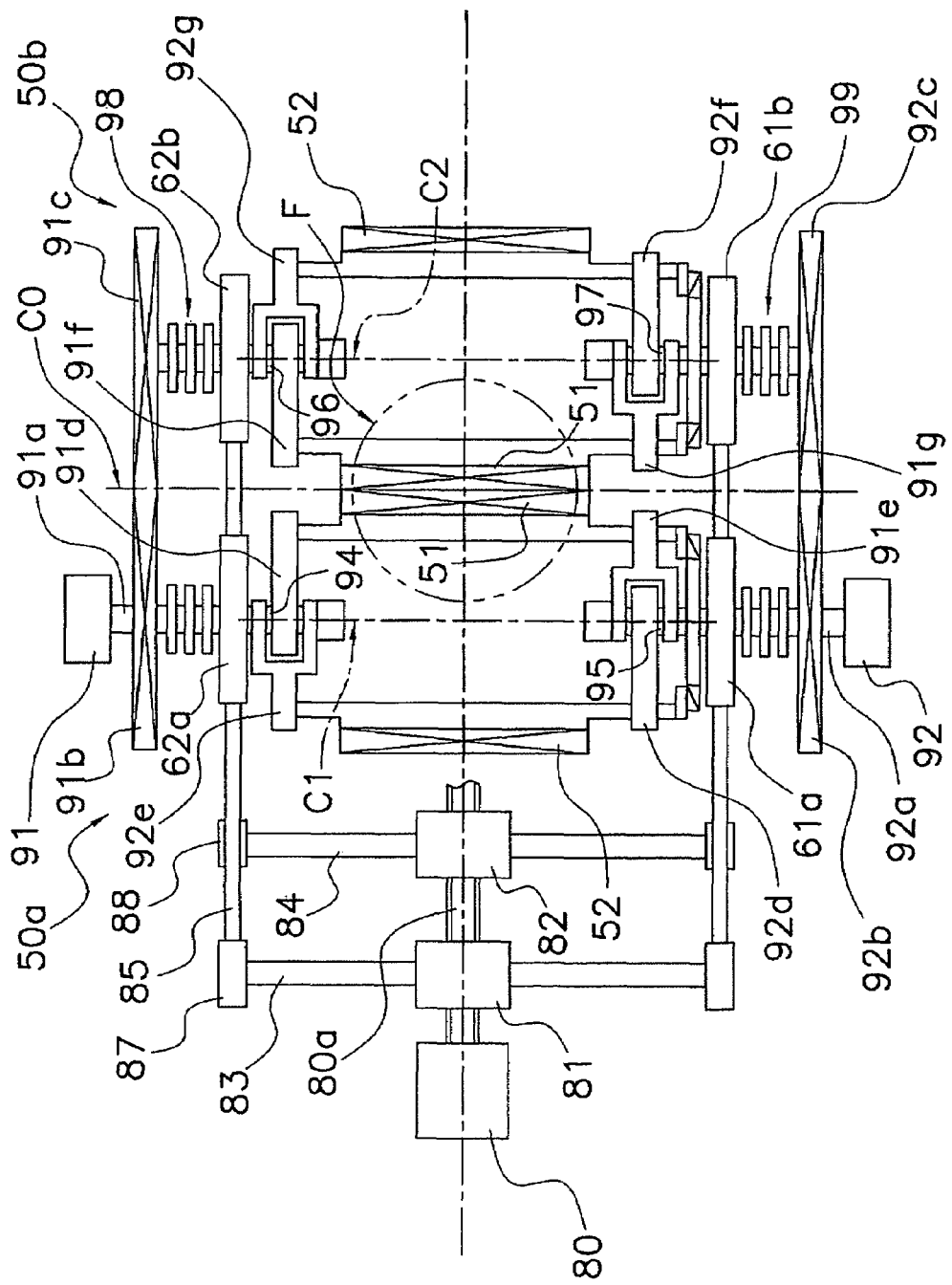
FIG. 4 is a plan view of the transverse sealing mechanism of the bag packaging system illustrated in FIG. 3 in accordance with the embodiment of the present invention.

The transverse sealing mechanism 17 is arranged below the forming mechanism 13, the pull-down belt mechanism 14, and the longitudinal sealing mechanism 15 and is supported by the support frame 12. As shown in FIGS. 3 and 4, the transverse sealing mechanism 17 includes left and right sealing jaw moving units 50a, 50b. The sealing jaw moving units 50a, 50b each revolve two sealing jaws 51, 52 through a D-shaped path, such that the two sealing jaw moving units 50a, 50b press the pair of sealing jaws 51 or the pair of sealing jaws 52 together while transversely sealing the tubular film. In the following description, the unit positioned on the left of the tubular film F as viewed in FIGS. 3 and 4 will be referred to as the first sealing jaw moving unit 50a and the unit positioned on the right will be referred to as the second sealing jaw moving unit 50b. The tubular film F is conveyed downward along a plane C0 that separates the two sealing jaw moving units 50a, 50b while being positioned such that the plane C0 is at the widthwise center of the tubular film F.

The sealing jaw moving units 50a, 50b each have a sealing jaw 51 and a sealing jaw 52, and the drive motor for the sealing jaws 51 and the drive motor for the sealing jaws 52 are separate entities. The sealing jaws 51 are driven by a drive motor 91 so as to rotate around axes C1 and C2. More specifically, the sealing jaw 51 of the first sealing jaw moving unit 50a rotates around the axis C1 and the sealing jaw 51 of the second sealing jaw moving unit 50b rotates around the axis C2. Meanwhile, the sealing jaws 52 are driven by a drive motor 92 so as to rotate around the axes C1 and C2. More specifically, the sealing jaw 52 of the first sealing jaw moving unit 50a rotates around the axis C1 and the sealing jaw 52 of the second sealing jaw moving unit 50b rotates around the axis C2.

The drive motor 91 rotates gears 91b, 91c and the rotation of the gears is transmitted through a Schmidt coupling 98 to revolution shafts 94, 96, which are coaxial with respect to the revolution axes C1, C2 of the sealing jaw moving units 50a, 50b. One end of a lever 91d is fixedly coupled to the revolution shaft 94 and one end of another lever 91f is fixedly coupled to the revolution shaft 96, such that the levers 91d, 91f rotate around the revolution axes C1, C2.

Meanwhile, the drive motor 92 rotates gears 92b, 92c and the rotation of the gears is transmitted through a Schmidt coupling 99 to revolution shafts 95, 97, which are coaxial with respect to the revolution axes C1, C2 of the sealing jaw moving units 50a, 50b. One end of a lever 92d is fixedly coupled to the revolution shaft 95 and one end of another lever 92f is fixedly coupled to the revolution shaft 97, such that the levers 92d, 92f rotate around the revolution axes C1, C2 respectively.

The sealing jaw 51 of the first sealing jaw moving unit 50a is supported at one end by the tip end of the lever 91d and at the other end by the tip end of the lever 91e. The lever 91e is a member that rotates around the revolution axis C1 and is supported such that it can rotate relative to the revolution shaft 95.

The sealing jaw 51 of the second sealing jaw moving unit 50b is supported at one end by the tip end of the lever 91f and at the other end by the tip end of the lever 91g. The lever 91g is a member that rotates around the revolution axis C2 and is supported such that it can rotate relative to the revolution shaft 97.

The sealing jaw 52 of the first sealing jaw moving unit 50a is supported at one end by the tip end of the lever 92d and at the other end by the tip end of the lever 92e. The lever 92e is a member that rotates around the revolution axis C1 and is supported such that it can rotate relative to the revolution shaft 94.

The sealing jaw 52 of the second sealing jaw moving unit 50b is supported at one end by the tip end of the lever 92f and at the other end by the tip end of the lever 92g. The lever 92g is a member that rotates around the revolution axis C2 and is supported such that it can rotate relative to the revolution shaft 96.

The sealing jaws 51, 52 are formed to be longer in the vertical direction of FIG. 4 than the diameter of the tubular film F and are provided with internal heating elements. The sealing surfaces of the sealing jaws 51, 52 are heated by the heating elements such that a portion of the tubular film F is thermally sealed when pinched between the left and right sealing jaws 51, 52.

Each of the Schmidt couplings 98, 99 includes three circular disks joined by links and serves as a shaft coupling that transmits the rotation of the input shaft to the output shaft. These Schmidt couplings 98, 99 can transmit the rotation of the input shaft to the output shaft even in situations where the output shaft moves in a direction perpendicular to the direction of the rotational axis of the input shaft such that the distance between the shaft cores of the input shaft and output shaft changes.

Figure 5:
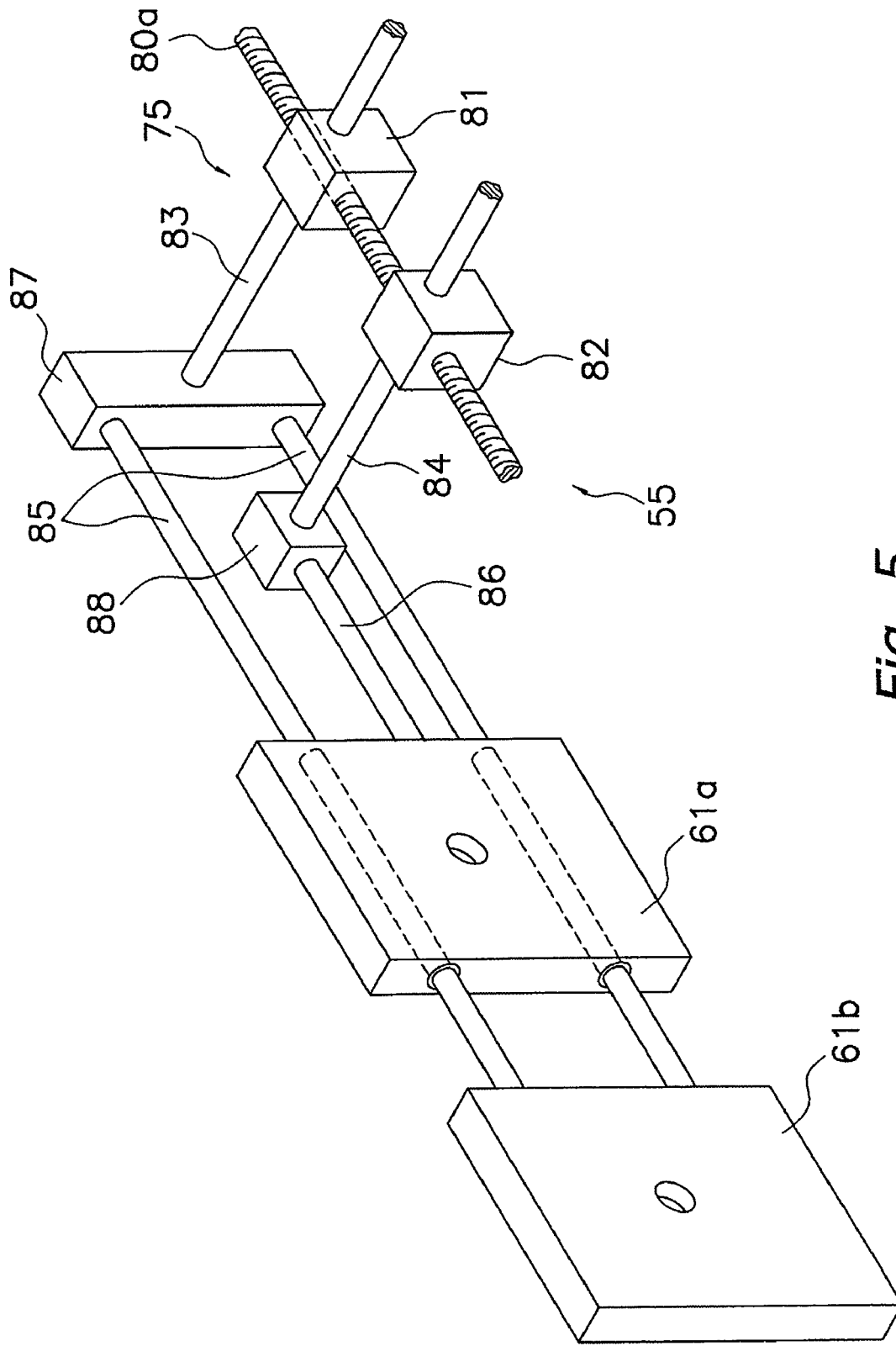
FIG. 5 is an explanatory partial view of a sideway drive mechanism of the bag packaging system in accordance with the embodiment of the present invention.

The revolution shafts 94, 95, 96, and 97 are pivotally supported by horizontal movement plates 62a, 61a, 62b, and 61b, respectively. The horizontal movement plates 62a, 61a, 62b, 61b are moved horizontally by a sideways drive mechanism 55 shown in FIG. 5. The horizontal movement plates 61a and 62a move together in the same manner and the horizontal movement plates 61b and 62b move together in the same manner. Here, the sideways drive mechanism 55 is described using the horizontal movement plates 61a and 61b as an example. As shown in FIG. 5, the sideways drive mechanism 55 has a drive mechanism 75 for moving the horizontal movement plates 61a, 61b closer to and away from each other, and a guide part or guide rail that supports the horizontal movement plates 61a, 61b such that they can slide freely relative to each other in the horizontal direction.

The drive mechanism 75 includes a ball screw 80a rotated by a servomotor 80 (see FIG. 3), first and second nut members 81, 82 that threadedly engage with the ball screw 80a, first and second linking rods 83, 84 that are arranged so as to intersect with the ball screw 80a at the right angle within a horizontal plane, a pair of third linking rods 85 arranged along the movement direction, and a fourth linking rod 86 arranged parallel to the third linking rods 85.

The first linking rod 83 is linked to the pair of third linking rods 85 through a coupling 87 and the tips of the pair of third linking rods 85 are fixedly coupled to a lateral end face of the horizontal movement plate 61b. The pair of third linking rods 85 penetrate through the horizontal movement plate 61a such that they can slide freely. The second linking rod 84 is linked to the fourth linking rod 86 through a coupling 88, and the tip of the fourth linking rod 86 is fixedly coupled to a lateral end face of the horizontal movement plate 61a.

The portion of the ball screw 80a that meshes with the first nut member 81 and the portion of the ball screw 80a that meshes with the second nut member 82 are threaded in the opposite directions. Thus, by rotating the ball screw 80a of the drive mechanism 75, the horizontal movement plates 61a, 61b can be made to approach each other or move away from each other.

Operations of the Bag Packager Prior to the Transverse Sealing Operation

Now the operation of the bag packaging system 1 will be described.

First, the operations implemented prior to the transverse sealing operation in the bag packaging system 1 are described with reference to FIG. 2.

The sheet-like film F delivered to the forming mechanism 13 from the film feeder 6 is wrapped around the tube 31 from the former 32 and formed into a tubular shape. The pull-down belt mechanism 14 conveys the tubular film downward. While the film F is wrapped onto the tube 31, the two edges of the tubular film overlap on the circumferential surface of the tube 31, and the overlapping portion is longitudinally sealed by the longitudinal sealing mechanism 15.

After the cylindrically-shaped tubular film F is sealed longitudinally, it passes through the tube 31 and moves down into the transverse sealing mechanism 17. Simultaneously with the movement of the tubular film F, the combination weighing machine 2 drops a batch of contents to be packaged through the tube 31 and into the tubular film F. Then, with the contents being inside the tubular film F, the transverse sealing mechanism 17 thermally seals a transverse portion of the tubular film F that correspond to the top end of a bag with contents and the bottom end of the subsequent bag located there-above.

Operations of the Bag Packaging System after the Transverse Sealing Operation

The bags manufactured in a continuous manner as described above drop to a conveyor belt 21 of the defect detector 20 from the transverse sealing mechanism 17 as shown in FIGS. 1 and 2, and the conveyor belt 21 conveys the bags downstream in the conveying direction to the post-process devices such as the seal checker 30 (post-processing devices).

Configuration of the Defect Detector

As shown in FIG. 2 and FIGS. 6 through 8, a defect detector 20 has the conveyor belt (an example of the first transfer unit) 21, a line sensor (an example of the detector) 22, a conveyor belt (an example of the second transfer unit)

23, and an air jet (an example of the remover) 24. The defect detector 20 checks the bags in order to find defects in the bags based on the signals issued by the defect detector 20 during such checking, while conveying the bags on the conveyor belts 21 and 23 of the bag packager 5 to the post-processing devices such as a seal checker 30. The defect detector 20 then removes the defective bags and the contents from the conveyance path.

As shown in FIG. 2, the conveyor belt 21 is arranged immediately below the transverse sealing mechanism 17 of the bag packager 5. The conveyor belt 21 receives the bags being dropped that are manufactured with contents packaged therein by the transverse sealing mechanism 17, and conveys such bags downstream. Additionally, as shown in FIGS. 6 through 9, the conveyor belt 21 includes an annular flat belt 21a that conveys objects, a drive roller 21b that supports the flat belt 21a from inside, a motor 21c that generates rotary drive force, and a timing belt 21d. The conveyor belt 21 conveys objects placed on the flat belt 21a to a desired direction when the rotary drive force of the motor 21c is transmitted to the drive roller 21b through the timing belt 21d and the flat belt 21a rotates.

Figure 9:
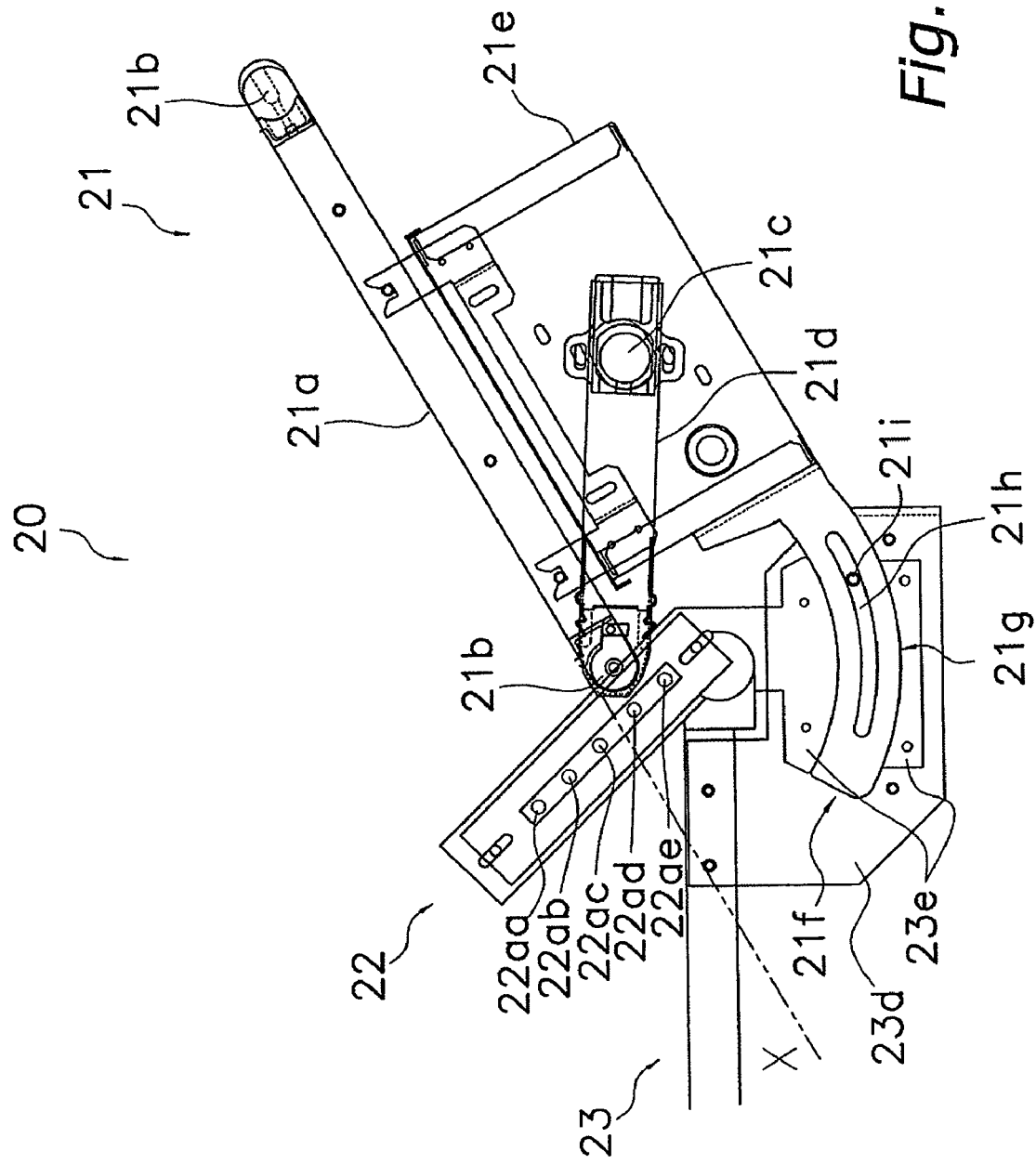
FIG. 9 is a side view of the defect detector of the bag packaging system illustrated in FIG. 6 in accordance with the embodiment of the present invention.

Further, as shown in FIG. 9, the conveyor belt 21 includes a motor box 21e that houses the motor 21c and the like inside, and a rotating frame 21f that is mounted to the downstream side of the motor box 21e.

The rotating frame 21f has a circular portion 21g that is supported pivotably between two boards 23e attached to a frame 23d of the conveyor be It 23, which will be described in detail later. The circular portion 21g is a plate member that is formed so as to contain two circular arcs of different radii having a rotary shaft of the drive roller 21b arranged downstream as the center. The circular portion 21g has a flute 21h formed thereon that is parallel to the two circular arcs. The flute 21h has a setscrew 21i inserted therein that can be screwed to an internal screw hole formed on the side of the frame 23d of the conveyor belt 23. The setscrew 21i is screwed at a desired position to secure the rotating frame 21f to the frame 23d of the conveyor belt 23 that is arranged on the downstream side of the conveyor belt 21. Consequently, by moving the circular portion 21g between the two boards 23e and securing it with the setscrew 21i, the whole conveyor belt 21 can be pivoted around the rotary shaft of the drive roller 21b which is arranged at downstream end of the conveyor belt 21 and serves as an imaginary rotary shaft, in order to adjust the angle of the conveyor belt 21 and the height of the upstream end of the conveyor belt 21. As a result, the angle of the conveyor belt 21 for receiving the bags and the distance between the position at which bags land onto the conveyor belt 21 and the transverse sealing mechanism 17 can be adjusted easily in accordance with the size and shape of the bags that are dropped from the transverse sealing mechanism 17 of the bag packager 5. This configuration results in a smooth conveyance of the bags that are dropped from the transverse sealing mechanism 17 to the downstream side, maintaining a certain posture of the bags without tipping the bags forward.

Figure 10:
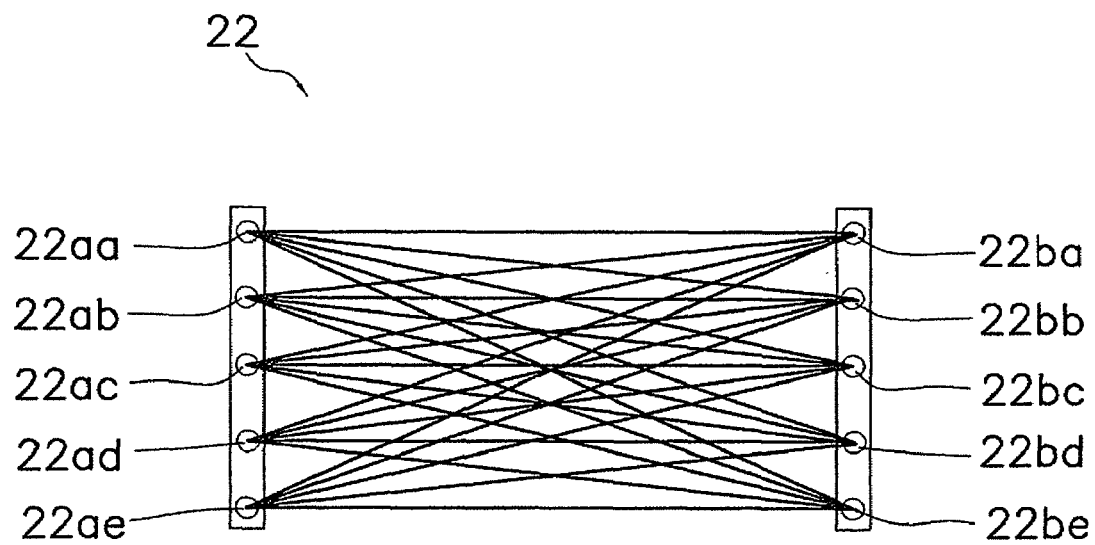
FIG. 10 is an explanatory view of the photoreceivers and projectors of the line sensor of the bag packaging system in accordance with the embodiment of the present invention.

As shown in FIG. 9, the line sensor 22 is arranged adjacent to the downstream end of the conveyor belt 21. In other words, the line sensor 22 is secured to the conveyor belt 23 so as to be situated adjacent to the drive roller 21b arranged at the downstream end of the conveyor 21. Additionally, the line sensor 22 has a plurality of projectors 22aa to 22ae and a plurality of photoreceivers 22ba to 22be that correspond to the plurality of projects 22aa to 22ae. As shown in FIG. 10, each of the photoreceivers 22ba to 22be receives light from each of the projectors 22aa to 22ae while each of the projects 22aa to 22ae emits light to all of the photoreceivers 22ba to 22be. At this point, when the bags to be conveyed on the conveyor belt 21 pass in front of the line sensor 22, that is, between the projectors 22aa to 22ae and the photoreceivers 22ba to 22be, some of the rays of light emitted from the projectors 22aa to 22ae are interrupted by the bags, and the amount of light to be received by the photoreceivers 22ba to 22be decreases. In this way, the decrease in the amount of light received by the photoreceivers 22ba to 22be indicates that there is an object on the conveyance path. Additionally, as shown in FIG. 9, among these projectors 22aa to 22ae and the photoreceivers 22ba to 22be, the projectors 22ad, 22ae and the photoreceivers 22bd, 22be that are arranged on the lower side are arranged below an imaginary surface X (see the chain double-dashed line indicated in FIG. 9) that is defined by extending the conveyance surface of the conveyor belt 21 to the downstream side, while all the other projectors 22aa to 22ac and the photoreceivers 22ba to 22bc are arranged above the imaginary surface X. As described above, by arranging an object detection sensor so as to cover both above and below the imaginary surface X that is defined by extending the conveyance surface of the conveyor belt 21 to the downstream side, it is possible to detect not only the bags being conveyed but also the contents that are spilled onto the conveyance path because of sealing failure in the transverse sealing mechanism 17 or the like. It should be noted that an ON signal will be sent to a controller 28 from the line sensor 22 when the line sensor 22 detects an object that is being conveyed as described above (see FIG. 12A to FIG. 12E).

The conveyor belt 23 is arranged immediately downstream of the conveyor belt 21. The conveyor belt 23 receives the bags from the conveyor belt 21 and conveys them to the post-processing devices such as the seal checker 30. Additionally, on the upstream side of the conveyor belt 23, that is, where the conveyor belt 23 is connected to the conveyor belt 21, the upstream end of the conveyor belt 23 is arranged to be below the downstream end of the conveyor belt 21. Because of this arrangement, a connecting portion of the conveyor belts 21 and 23 is formed as a step portion. The above-mentioned line sensor 22 is arranged on this step portion, thus enabling detection of not only the bags but also the contents of the bags such as chips and the like that drop from the conveyor belt 21.

Figure 6:
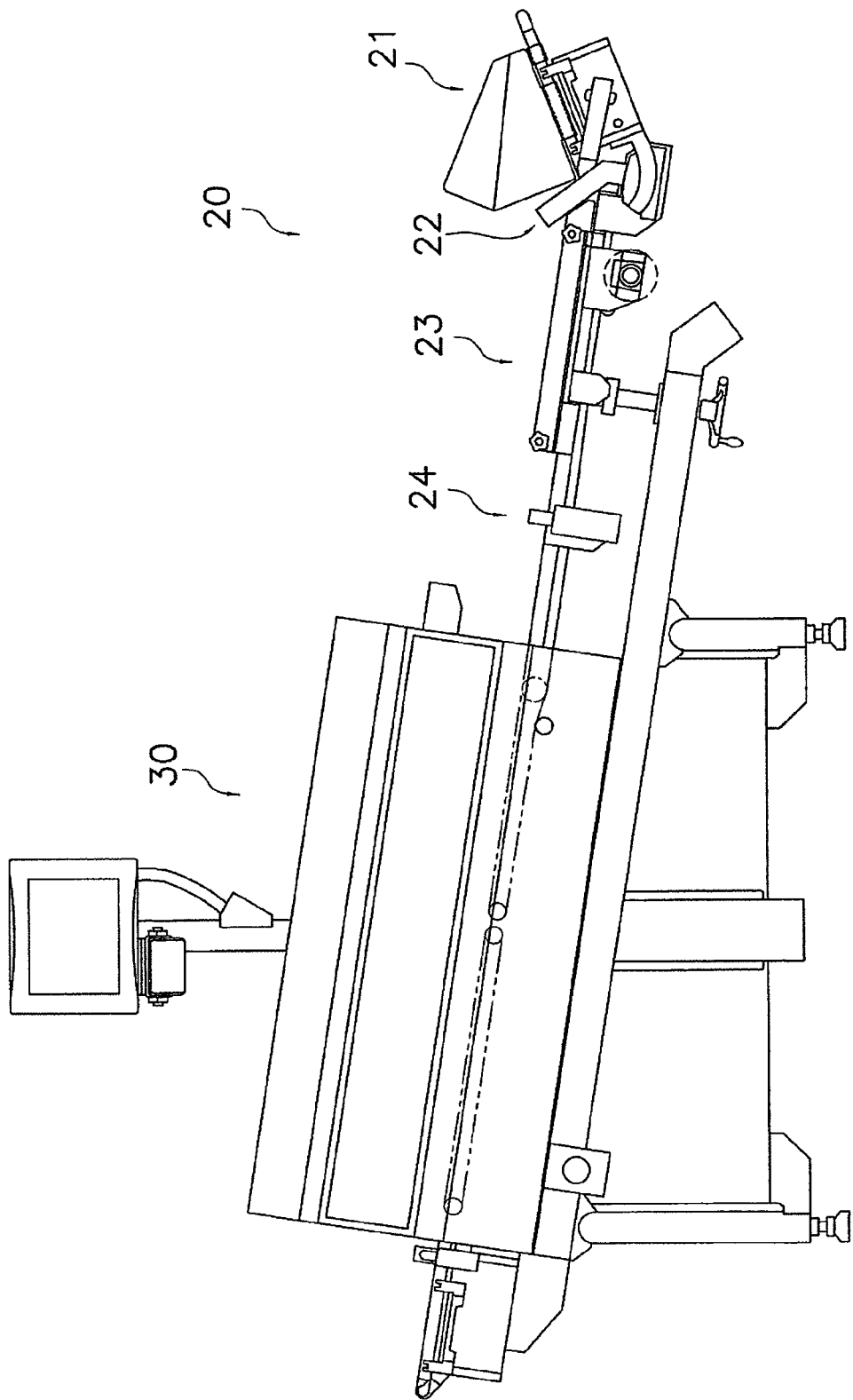
FIG. 6 is a side view of a defect detector included of the bag packaging system in accordance with the embodiment of the present invention.
Figure 7:
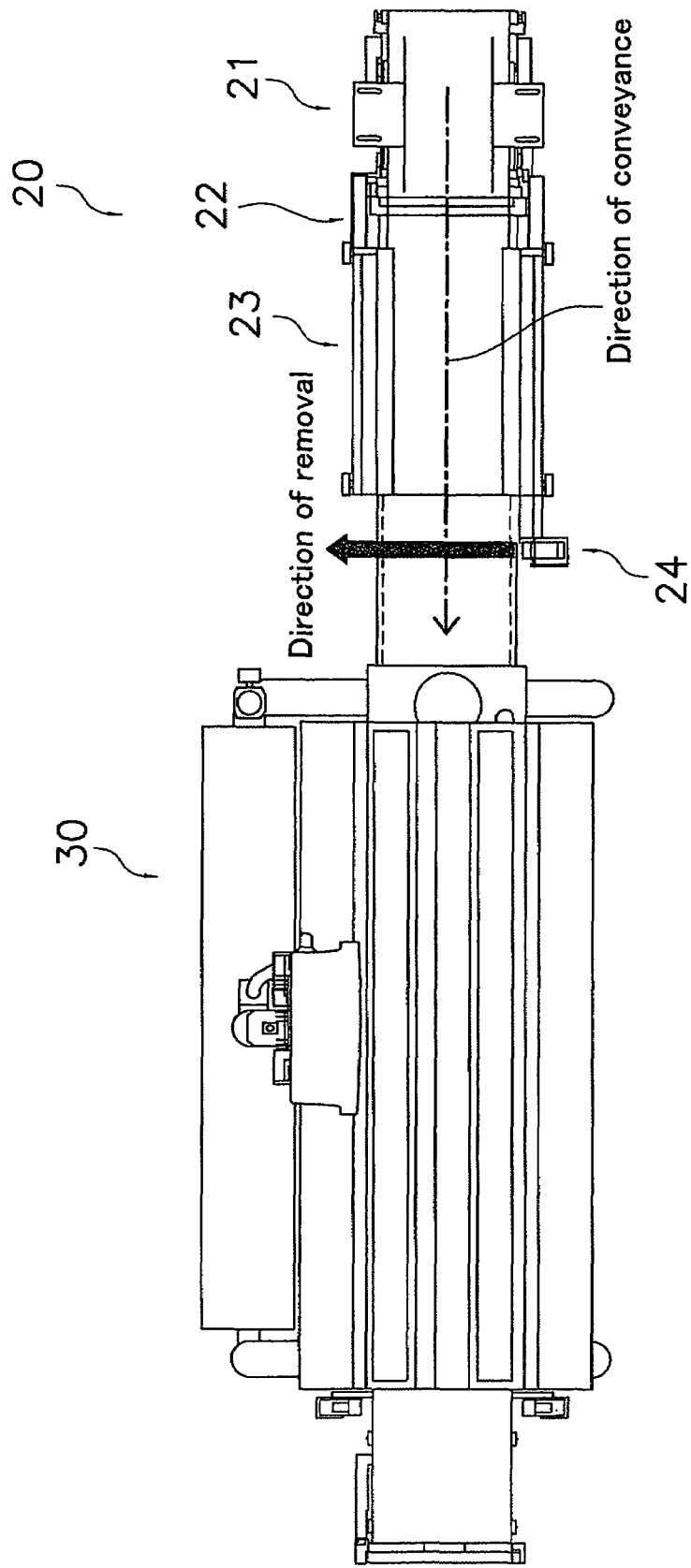
FIG. 7 is a plan view of the defect detector of the bag packaging system illustrated in FIG. 6 in accordance with the embodiment of the present invention.

As shown in FIG. 6, the air jet 24 is arranged in the middle portion of the conveyor belt 23, halfway before the bags are conveyed to the post-processing devices such as the seal checker 30. As shown in FIG. 7, the air jet 24 blows air from a direction substantially perpendicular to the conveying direction onto the bags and bag contents such as chips that are determined to be defective by a controller 28, which will be described later, based on the results of object detection implemented by the line sensor 22. Consequently, the defective bags and the contents can be removed from the conveyance path before they are conveyed to the post-processing devices.

Control Block

Figure 11:
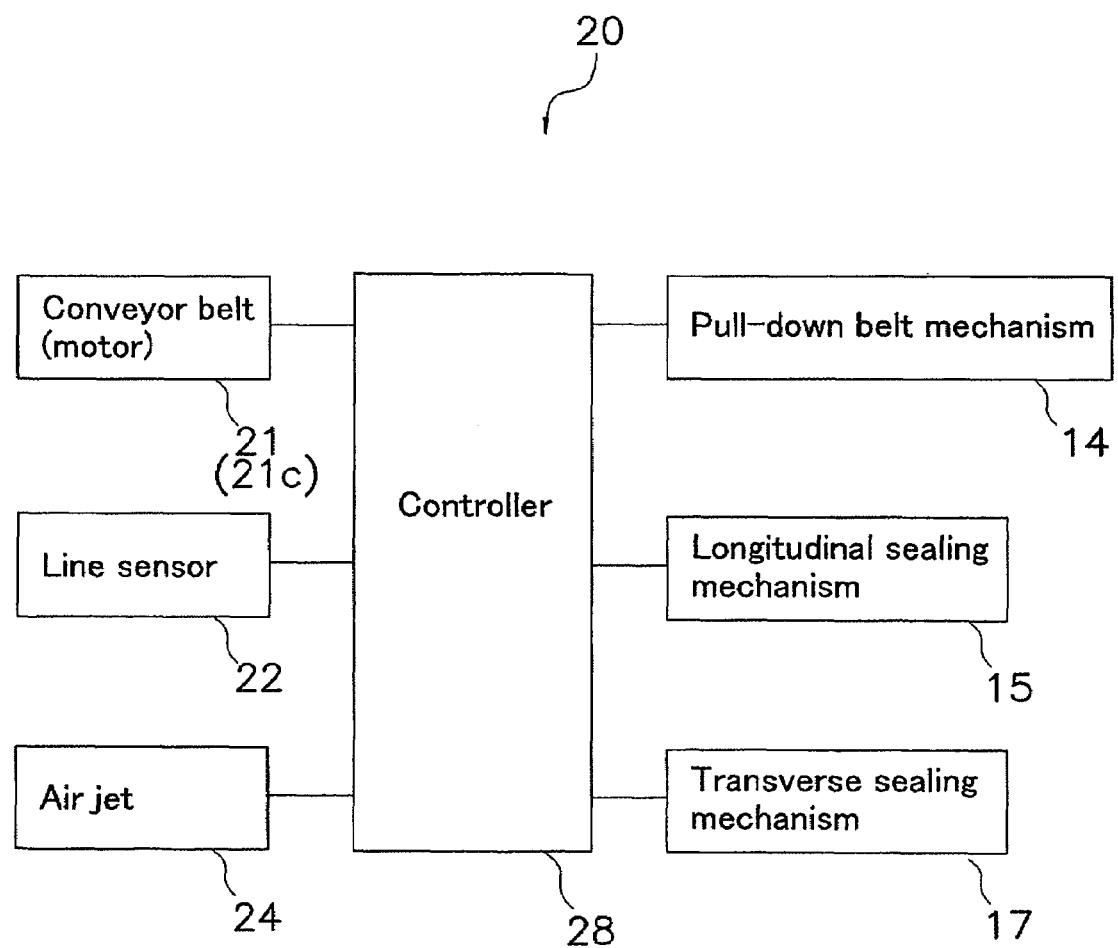
FIG. 11 is a control block diagram of the bag packaging system illustrated in FIG. 1 in accordance with the embodiment of the present invention.

The bag packaging system 1 according to this embodiment includes the controller 28, which includes a control block as shown in FIG. 11. The controller 28 is operatively connected to the conveyor belts 21 and 23 and the line sensor 22, and preferably includes a microcomputer with a control program that find defective bags as discussed below. The controller 28 can also include other conventional components such as an input interface circuit, an output interface circuit, and storage devices such as a ROM (Read Only Memory) device and a RAM (Random Access Memory) device.

As shown in FIG. 11, the controller 28 is operatively connected to the pull-down belt mechanism 14, the longitudinal sealing mechanism 15, the transverse sealing mechanism 17, the conveyor belt 21 (motor 21c), the line sensor 22, and the air jet 24. The controller 28 controls the pull-down belt mechanism 14, the longitudinal sealing mechanism 15 and the transverse sealing mechanism 17, which are included in the bag packager 5, in accordance with the operational setting conditions. The controller 28 determines whether or not the bags being conveyed are defective based on the pre-input size of the bags to be manufactured by the bag packager 5, the conveying speed of the conveyor belt 21, and the duration of time during which the line sensor 22 transmitted the detection signal.

Defect Detection by the Back Packaging System

The bag packaging system 1 according to this embodiment implements defect detection to detect the defective bags among the bags manufactured by the bag packager 5. It should be noted that the defects of the bags described here include a defect in which contents of a bag are discharged onto the conveyor belt 21 due to a sealing failure during the longitudinal sealing mechanism 15 or the transverse sealing mechanism 17, and a defect in which the bags, which should be conveyed at predetermined intervals after being manufactured by the bag packager 5, are conveyed immediately one after another. Further, the defect detector 20 also detects bags of irregular sizes, such as a double bag (a bag having a length of two bags) that is manufactured automatically by the bag packager 5 when a metal detector that is provided between the weighing process and the packaging process reacts, and a bag having wrong length and or wrong size due to a setting error.

Specifically, in the bag packaging system 1, the size (length in the conveying direction) of the bags to be manufactured by the bag packager 5 is first input by an operator through the operating switch 7. The input bag size is stored in a memory, which is not shown in the figures.

When the bag packaging system 1 starts operating, the conveying speed of the conveyor belt 21 (rotating speed of the motor 21c) is transmitted to the controller 28. Subsequently, the bags that are discharged from the transverse sealing mechanism 17 of the bag packager 5 onto the conveyor belt 21 and conveyed downstream are detected by the line sensor 22 arranged at the connecting portion between the conveyor belts 21 and 23. Then this detection time (duration of any of rays of the light emitted to the photoreceivers 22ba to 22be from the projectors 22aa to 22ae being interrupted in the line sensor 22) is transmitted from the line sensor 22 to the controller 28. It should be noted that an ON signal or the detection signal will be sent to the controller 28 from the line sensor 22 when the line sensor 22 detects an object that is being conveyed as described above (see FIG. 12A to FIG. 12E). Therefore, the detection time is also the duration of the detection signal.

Here, the controller 28 determines whether there is any defective bag based on the above-mentioned bag size, the conveying speed, and the detection time. Specifically, the controller 28 makes a comparison between the detection time in the case a bag having the proper size is detected, which is calculated based on the size of the proper bag that should be manufactured by the bag packager 5 and the conveying speed of the conveyor belt 21, and the actual detection time based on the detection signals from the line sensor 22. When the actual detection time is within a predetermined range (an example of the proper detection time range), that is, within predetermined limits (see FIG. 12A) from the proper detection time range, the bag detected by the line sensor 22 is determined to be a proper bag. On the other hand, if the actual detection time is beyond the predetermined limits and longer (see FIG. 12B) or shorter (see FIG. 12C) than the above-mentioned proper detection time range, the controller 28 determines that the bags are not being manufactured properly by the bag packager 5.

Figure 12A:
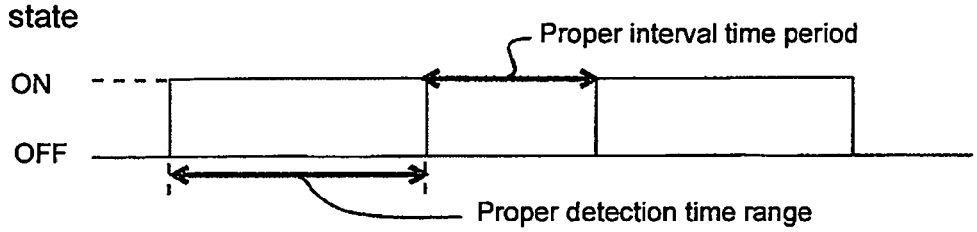
FIGS. 12A-E are schematic diagrams of the detection signals to be transmitted from the line sensor to a controller of the bag packaging system in accordance with the embodiment of the present invention.
Figure 12B:
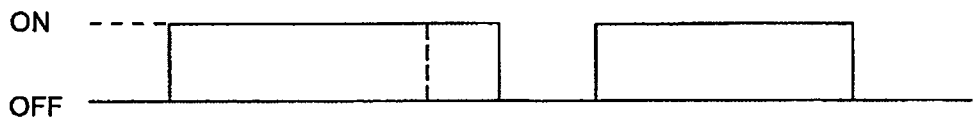
Figure 12C:
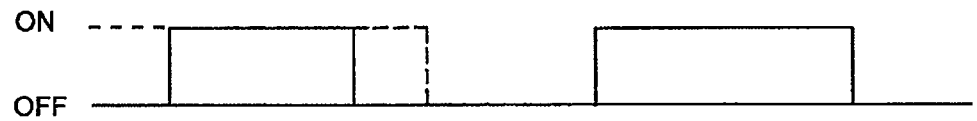
Figure 12D:
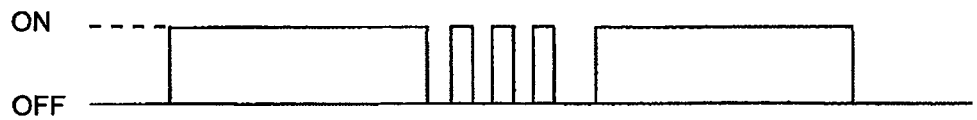

Additionally, when, for example, a sealing failure takes place in the transverse sealing mechanism 17, the contents to be packaged in a bag may spill from the bag onto the conveyor belt 21. The bag packaging system 1 according to this embodiment can detect not only the above-mentioned defective bags that are caused by the bag-packaging failure, but also the contents that are spilled from their bags onto the conveyor belt 21 as they are being conveyed because of the sealing failure. Specifically, if the line sensor 22 detects an object for considerably a short period of time compared to the proper detection time period, (see FIG. 12D), it is determined that the contents of a bag are spilled onto the conveyor belt 21 and the bags in front and behind the detected contents are determined as defective. It should be noted that, when spilled contents are detected as shown in FIG. 12D, either both of the bags in front and behind the detected contents as described above, or only one bag either in front or behind can be determined as being defective.

Figure 12E:
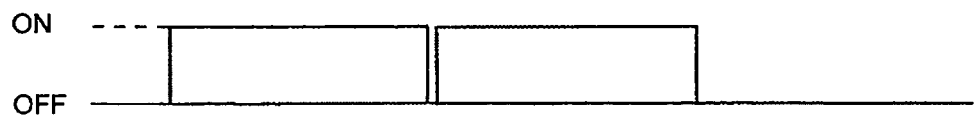

Further, besides the bags of irregular sizes (see FIGS. 12B and 12C), the bags that are conveyed at a narrow interval between them as shown in FIG. 12E are also determined as being defective. In this case, the controller 28 calculates the proper interval time period based on the pre-input proper bag size and the conveying speed of the conveyor belt 21. This is to prevent a problem that happens when the bags that should be conveyed at predetermined intervals are conveyed at narrow intervals one after another as shown in FIG. 12E, because it makes it impossible for the post-processing devices such as the seal checker 30 to process the bags properly. When such defect is detected, the controller 28 controls the air jet 24 to remove only the later-conveyed bag that is responsible for the narrow interval.

The results of determination by the controller 28 are reflected in the control of air jet timing of the air jet 24. In other words, as shown in FIG. 7, the bags determined as defective by the controller 28 and the contents detected by the line sensor 22 are removed from the conveyance path in a predetermined direction by the air blown from the air jet 24 when such defective bags and contents are conveyed to the position in front of the air jet 24.

Characteristics of Back Packaging System (1) As shown in FIGS. 6 and 7, the bag packaging system 1 according to this embodiment includes the defect detector 20 that detects defects of the bags caused by bag packaging failure in the bag packager 5. This defect detector 20 includes the conveyor belt 21 that is disposed below the bag packager 5, the conveyor belt 23 that is disposed immediately downstream of the conveyor belt 21, and the line sensor 22 that is disposed at the step portion at the connecting portion between the conveyor belts 21 and 23. The line sensor 22 determines whether or not the bags that passed in front of the line sensor 22 are defective based on the results of detection of objects conveyed from the conveyor belt 21 to the conveyor belt 23. The results specifically include the detection time from the line sensor 22, the pre-input length of the bags, and the conveying speed of the conveyor belt 21.

In this way, defects of the bags are determined based on the results of detection by the line sensor 22 that is arranged adjacent to the conveyor belt 21, which is disposed immediately below the bag packager 5. As a result, before the bags discharged from the bag packager 5 are conveyed to the post-processing devices such as the seal checker 30, the defective bags are promptly removed from the conveyance path. Consequently, this prevents the defective bags from being unnecessarily conveyed to and processed by the post-processing devices such as the seal checker 30, thus improving the efficiency of the process. Additionally, since a simple sensor that only detects objects that are conveyed is used to determine defects, it is possible to detect the defective bags without much increase in the cost. Further, since the contents of the bags and the like can be removed from the conveyance path promptly, even if, for example, snack foods contents such as potato chips are spilled onto the conveyance path because of sealing failure, soiling of the conveyance path with the oil can be avoided. This prevents problems that arise when the conveyance path is soiled with oil, such as the bags slipping and not being able to keep the predetermined internal. The present invention is effective especially when the conveyance path is tilted upwardly as it leads to the downstream side and the bags are conveyed upwards as shown in FIG. 2, since the bags in such conveyance path tend to slip easily as they are conveyed.

Figure 8:
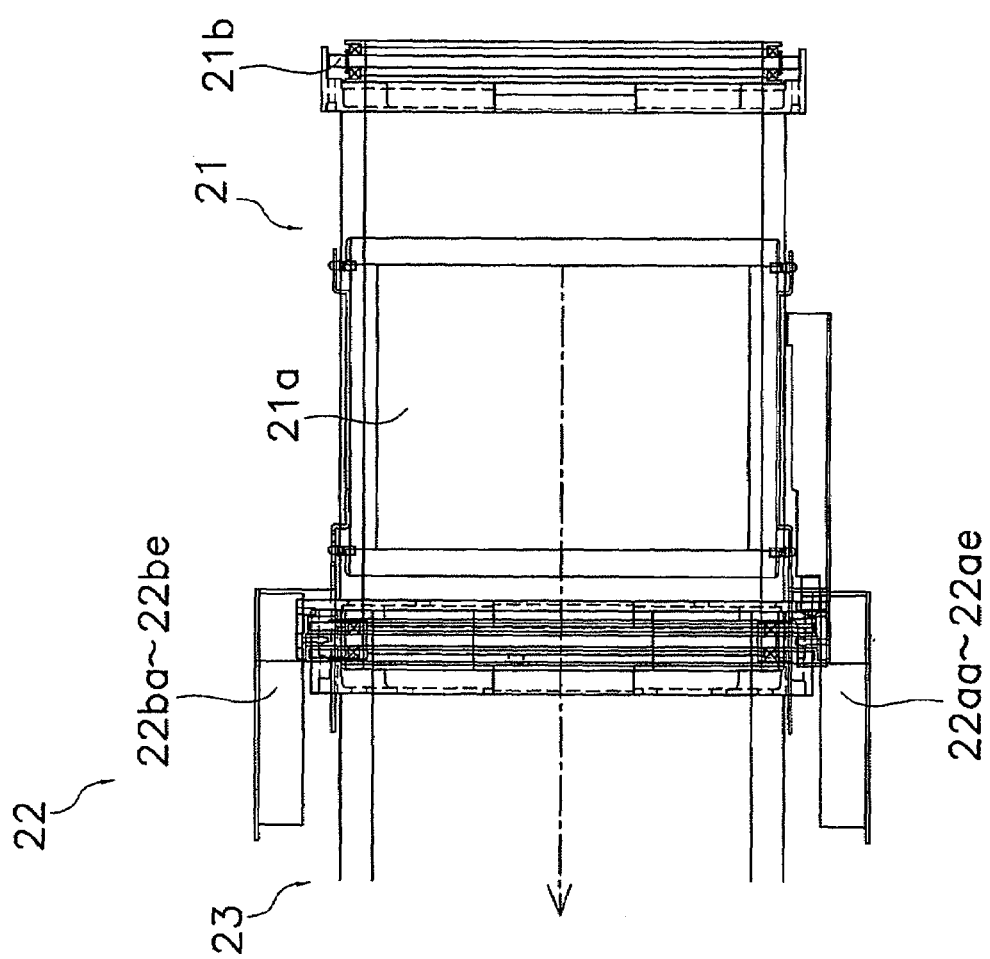
FIG. 8 is an enlarged plan view of the connecting portion between the conveyor belts of the defect detector of the bag packaging system illustrated in FIG. 6 in accordance with the embodiment of the present invention.

(2) As shown in FIGS. 8 and 9, in the bag packaging system 1 according to this embodiment, the line sensor 22, which detects objects that are conveyed, is arranged at the connecting portion between the conveyor belts 21 and 23 that convey the manufactured bags. This line sensor 22 has a plurality of projectors 22aa to 22ae and a plurality of photoreceivers 22ba to 22be, with part of the projectors and the photoreceivers (projectors 22ad, 22ae, and photoreceivers 22bd, 22be) being arranged below the imaginary surface X that is defined by extending the conveyance surface of the conveyor belt 21 to the downstream side. Additionally, other projectors and photoreceivers (projectors 22aa to 22ac and photoreceivers 22ba to 22bc) are arranged above the above-mentioned imaginary surface X.

This configuration enables the projectors 22aa to 22ac and the photoreceivers 22ba to 22bc to detect the bags, while the projectors 22ad, 22ae and the photoreceivers 22bd, 22be detect the contents spilled from their bags onto the conveyance due to sealing failure and the like.

(3) As shown in FIG. 7, in the bag packaging system 1 according to this embodiment, the conveyor belt 21 that is positioned immediately below the transverse sealing mechanism 17 of the bag packager 5 and the conveyor belt 23 that is connected immediately downstream of the conveyor belt 21 form the conveyance path of the bag packaging system 1.

This configuration results in an efficient conveyance of the manufactured bags to the post-processing devices such as the seal checker 30.

(4) As shown in FIG. 9, in the bag packaging system 1 according to this embodiment, the downstream end of the conveyor belt 21 is arranged so as to be above the upstream end of the conveyor belt 23.

This configuration enables formation of a step portion at the connecting portion between the conveyor belts 21 and 23. Thus, placing the line sensor 22 along this step portion results in an easy detection of both the bags and the contents.

(5) As shown in FIG. 8, in the bag packaging system 1 according to this embodiment, the line sensor 22 that is arranged such that a plurality of projectors 22aa to 22ae and a plurality of photoreceivers 22ba to 22be sandwich the conveyance path is used to detect the passage of objects.

This configuration enables determination of defects of the bags with an inexpensive and simple sensor.

(6) As shown in FIG. 9, in the bag packaging system 1 according to this embodiment, the conveyor belt 21 that includes the flat belt 21a, the motor 21c and the like is used as a conveyance mechanism (first transfer unit) that receives the bags discharged from the transverse sealing mechanism 17 and conveys them downstream.

This configuration enables control of the conveying speed, which provides a more accurate determination of defects as compared to a case where a chute is used as a conveyance mechanism (first transfer unit). Further, since the conveyor belt 21 forcibly conveys the bags to the downstream side, bags do not get stuck during the conveyance, which happens when a chute is used. Therefire, the bags to be conveyed smoothly to the downstream side without disturbing the posture of the bags.

(7) As shown in FIG. 9, in the bag packaging system 1 according to this embodiment, the conveyor belt 21 has the rotating frame 21f. By moving the circular portion 21g of the rotating frame 21f between the two boards 23e that are secured to the conveyor belt 23 side, the conveyor belt 21 can pivot around the vicinity of the downstream end of the conveyor belt 21. Consequently, if it is desired to adjust the height of the conveyor belt 21 according to the size of bags to be manufactured by the bag packager 5, the height of the upstream end of the conveyor belt 21 can be adjusted and the bags can be conveyed smoothly regardless of the bag size.

Additionally, since the conveyor belt 21 is rotated around the vicinity of the downstream end thereof, there are hardly any changes to the relative position of the conveyor belt 21 with respect to the line sensor 22 that detects objects that are being conveyed, which results in a stable detection by the line sensor 22.

Further, since the angle of the conveyor belt 21 for receiving dropping bags can also be adjusted, a stable conveyance can be achieved to prevent tipping of the bags and irregular intervals (pitch misalignment) between the bags.

(8) As shown in FIG. 7, in the bag packaging system 1 according to this embodiment, the air jet 24 that blows air onto objects that are subject to removal is used as a remover to remove the bags that are determined as defective by the controller 28.

This configuration results in an easy removal of not only the bags but also the contents such as snack foods from the conveyance path. Consequently, the bags determined as defective and the contents are prevented from being conveyed to the post-processing devices. Accordingly, unnecessary process for the defective bags can be avoided.

Other Embodiments

While only one embodiment of the present invention has been explained, the scope of the invention is not limited to the above-described embodiment, and various changes and modifications can be made herein without departing from the scope of the invention.

(A) The above-mentioned embodiment is explained with an example in which the line sensor 22 is positioned at the connecting portion of the conveyor belts 21 and 23 to determine defects of the bags through object detection by the line sensor 22. However, the present invention is not limited to the configuration of the above-mentioned example.

In other words, as long as the line sensor 22 is provided at the downstream end of the conveyor belt 21, there is no need for the other conveyor belt 23 arranged downstream of the conveyor belt 21. However, as in the above-mentioned embodiment, it is more preferable to convey the bags to the post-processing devices through the conveyor belt 23 as well as the conveyor belt 21, since the bags that are determined to be defective can be removed from the conveyance path while they are being conveyed on the conveyor belt 23, that is, before such defective bags reach the post-processing devices.

(B) The above-mentioned embodiment is explained with an example in which the line sensor 22 that has a plurality of projectors 22aa to 22ae and a plurality of photoreceivers 22ba to 22be is used as the detector that detects the defective bags and the contents spilled onto the conveyance path because of sealing failure. However, the present invention is not limited to the above-mentioned example.

For example, as a detector, a different sensor such as an infrared ray sensor can be used as long as such sensor is capable of detecting objects that are being conveyed.

However, as in the above-mentioned embodiment, having the line sensor 22 that has a plurality of projectors 22aa to 22ae and a plurality of photoreceivers 22ba to 22be is more preferable in terms of higher detection sensitivity of the line sensor 22 and easier detection of the contents (such as the crumbs of snack foods) that are spilled onto the conveyance path because of bag sealing failure.

It should be noted that if a sensor for jammed crumbs is provided in the transverse sealing mechanism 17, such sensor for jammed crumbs can detect the contents that are spilled onto the conveyance path. Therefore, in such a case, a sensor having one projector and one photoreceiver can be used as the detector.

(C) The above-mentioned embodiment is explained with an example in which defects of the bags are determined by transmitting the conveying speed of the conveyor belt 21 to the controller 28. However, the present invention is not limited to the above-mentioned example.

For example, the conveying speed of the conveyor belt 23 can be transmitted to the controller 28 such that defects are determined based on the conveying speed of the conveyor belt 23 as well as the conveying speed of the conveyor belt 21. Because of this, if the length of a bag is extremely long and its tip is already reaching the conveyor belt 23 while the bag is being detected by the line sensor 22, the bag will be conveyed at the conveying speed of the conveyor belt 23. Therefore, transmitting the conveying speed of the conveyor belt 23 as well as that of the conveyor belt 21 to the controller 28 provides a more accurate determination of defects regardless of the bag size.

(D) The above-mentioned embodiment is explained with an example of using the air jet 24 as a means to remove the defective bags and the contents that are spilled onto the conveyance path from the conveyance path. However, the present invention is not limited to the above-mentioned example.

For example, in order to mechanically remove objects from the conveyance path, a remover that can move back and forth across the conveyance path by a cylinder and the like can be used.

Additionally, a mechanism such as a drop-down conveyor belt that is tilted downward in order to remove defective bags can be used as a removal mechanism.

According to the defect detection device of the present invention, a defect in a bag can be detected after such defective bags are discharged from the bag packaging machine. Thus, it is possible to detect the defective bags at an early point. This prevents the defective bags from being unnecessarily conveyed to and processed by the post-processing devices such as a seal checker downstream, thus improving the efficiency of the process.

Since the defect detection device of the present invention successfully achieves a prompt detection of sealing failure and conveyance failure at a relatively early point after the bags are discharged from the bag packaging machine, the present invention is widely applicable to bag packaging machines provided with a conveyor that conveys the manufactured bags downstream.

As used herein, the following directional terms "forward, rearward, above, downward, vertical, horizontal, below and transverse" as well as any other similar directional terms refer to those directions of a device equipped with the present invention. Accordingly, these terms, as utilized to describe the present invention should be interpreted relative to a device equipped with the present invention.

The term "configured" as used herein to describe a component, section or part of a device includes hardware and/or software that is constructed and/or programmed to carry out the desired function.

Moreover, terms that are expressed as "means-plus function" in the claims should include any structure that can be utilized to carry out the function of that part of the present invention.

The terms of degree such as "substantially", "about" and "approximately" as used herein mean a reasonable amount of deviation of the modified term such that the end result is not significantly changed. For example, these terms can be construed as including a deviation of at least +5% of the modified term if this deviation would not negate the meaning of the word it modifies.

This application claims priority to Japanese Patent Application No. 2004-153522. The entire disclosure of Japanese Patent Application No. 2004-153522 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A defect detection device adapted to receive bags manufactured by a bag packaging machine and convey the bags to a downstream side through a conveyance path while checking for defects of the bags, the defect detection device comprising:

a first transfer unit that is arranged below the bag packaging machine and adapted to receive the bags that are discharged from the bag packaging machine and convey the bags to a downstream side;

a second transfer unit that is arranged on the downstream side of the first transfer unit;

a detector that is arranged adjacent to a downstream end of the first transfer unit and configured to send a detection signal when the detector detects an object that is conveyed by the first transfer unit; and a controller that is operatively connected to the first transfer unit, the detector, and the second transfer unit, and stores therein a size of a proper bag that is being manufactured, the controller being configured to find a defective bag based on the size of the proper bag, a conveying speed of the first transfer unit, duration of the detection signal from the detector, and a conveying speed of the second transfer unit, the first transfer unit being pivotably supported by the second transfer unit.

2. The defect detection device according to claim 1, wherein the detector is arranged so as to be partially below and partially above a conveyance surface of the first transfer unit.

3. The defect detection device according to claim 1, wherein the downstream end of the first transfer unit is arranged so as to be above an upstream end of the second transfer unit.

4. The defect detection device according to claim 1, wherein the detector is a line sensor that has a plurality of projectors and a plurality of photoreceivers that are arranged such that the object conveyed by the first transfer unit passes between the plurality of projectors and the plurality of photoreceivers.

5. The defect detection device according to claim 1, wherein the first transfer unit has a conveying belt that conveys the object and a motor that rotates the conveying belt.

6. The defect detection device according to claim 1, further comprising a remover that is adapted to remove the object from the conveyance path when the controller finds a defective bag.

7. The defect detection device according to claim 6, wherein the remover is adapted to remove the object from the conveyance path by blowing air onto the object.

8. The defect detection device according to claim 6, further comprising a second transfer unit that is arranged on the downstream side of the first transfer unit, wherein the remover is adapted to remove the object from the conveyance path while the object is being conveyed by the second transfer unit.

9. The defect detection device according to claim 1, wherein the first transfer unit is supported to the second transfer unit so as to be pivotable around the downstream end of the first transfer unit.

10. The defect detection device according to claim 1, wherein the controller is configured to calculate a proper detection time range based on the size of the proper bag and the conveying speed of the first transfer unit, and the controller is configured to find a defective bag when the duration of the detection signal is either longer or shorter than the proper detection time range.

11. The defect detection device according to claim 1, wherein the controller is configured to calculate a proper interval time period based on the size of the proper bag and the conveying speed of the first transfer unit, and the controller is configured to find a defective bag when an interval between the detection signals is shorter than the proper interval time period.

12. A bag packaging system comprising:

a bag packaging machine that manufactures bags by sealing a sheet-like package paper and forming bags with contents contained therein; and the defect detection device according to claim 1 that is designed to receive bags manufactured by the bag packaging machine and convey the bags to a downstream side through a conveyance path while checking for defects of the bags.

\* \* \* \* \*